US00PP12465P2

(12) United States Plant Patent
Olesen et al.

(10) Patent No.: US PP12,465 P2
(45) Date of Patent: Mar. 19, 2002

(54) HYBRID TEA ROSE PLANT NAMED 'POULRIM'

(76) Inventors: L. Pernille Olesen; Mogens N. Olesen, both of Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/277,236

(22) Filed: Mar. 26, 1999

(51) Int. Cl.[7] ..... A01H 5/00
(52) U.S. Cl. ..... Plt./135
(58) Field of Search ..... Plt./130, 135, 136

(56) References Cited

U.S. PATENT DOCUMENTS

PP5,177 P * 1/1984 Christensen ..... Plt./15
PP8,861 P * 8/1994 Starkl ..... Plt./16

OTHER PUBLICATIONS

UPOV–ROM GTITM Computer Database 2000/06, Dec. 8, 2000, GTI Jouve Retrieval Software, citation for 'Poulrim'.*

* cited by examiner

*Primary Examiner*—Bruce R. Campell
*Assistant Examiner*—June Hwu

(57) ABSTRACT

A new hybrid tea rose plant which has abundant, non-fading, apricot/bronze-colored flowers and attractive, disease resistant foliage. This new and distinct variety has shown to be uniform and stable in the resulting generations from asexual propagation.

2 Drawing Sheets

SUMMARY OF THE INVENTION

The present invention constitutes a new and distinct variety of a hybrid tea rose plant which originated from a controlled crossing between two unnamed, non-commercial, non-patented seedlings. The two parents were crossed and the resulting seeds were planted in a controlled environment. The new variety is named 'POULrim'.

The new rose may be distinguished from its seed parent, an unnamed seedling, by the following combination of characteristics:

1. The seed parent's blooms have no fragrance; whereas 'POULrim' has a moderately strong fragrance;

2. The seed parent's blooms are dark bronze in color; whereas, 'POULrim' has lighter bronze to apricot blooms.

3. The seed parent has typically very single blooms; whereas; 'POULrim' typically has 1–5 flowers per stem.

The new variety may be distinguished from its pollen parent, an unnamed seedling, created by the same inventors, by the following combination of characteristics:

1. The pollen parent is classified as a floribunda rose; whereas, 'POULrim' is a hybrid tea rose;

2. The color of the pollen parents blooms is amber-yellow compared to 'POULrim's' blooms which are more apricot/bronze colored.

The objective of the hybridization of this rose variety for garden use was to create a new and distinct variety with unique qualities, such as:

1. Uniform and abundant flowers;
2. Vigorous and compact growth;
3. Disease resistance;
4. Fragrance;
5. Continuous blooming.

This combination of qualities is not present in previously available commercial cultivars of this type and distinguishes 'POULrim' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULrim' was selected in spring, 1989 by the inventors as a single plant from the progeny of the aforementioned hybridization Asexual reproduction of 'POULrim' by traditional budding was first done by L. Pernille and Mogens N. Olesen in August 1989, in their nursery in Fredensborg, Denmark. This initial and other subsequent propagations conducted in controlled environments have demonstrated that the characteristics of 'POULrim' are true to type and are transmitted from one generation to the next.

BRIEF DESCRIPTION OF THE DRAWING

The accompanying color illustration shows, as true as is reasonably possible to obtain in color photographs of this type, the typical characteristics of the buds, flowers, leaves, and stems of 'POULrim'.

Specifically illustrated in SHEET 1:

1. Stem showing branching and the attachment of leaves, buds, and peduncles;

2. Flower bud, partially opened bud, and open bloom;

3. Flower petals, detached;

Specifically illustrated in SHEET 2:

4. Sepals, receptacle, and pedicel;

5. Flowering stem as well as a bare stem exhibiting thorns;

6. Leaves.

DETAILED DESCRIPTION OF THE VARIETY

The following is a description of 'POULrim' as observed in its growth in a field nursery in Jackson County, Oreg., on plants aged eighteen months. Color references are made using The Royal Horticultural Society (London, England) Colour Chart, 1995, except where common terms of color are used.

For a comparison, several physical characteristics of the rose variety 'POULbero', a hybrid tea rose variety, from the same inventors, described and illustrated in U.S. Plant Pat. No. 8,230 and issued on May 18, 1993 are compared to 'POULrim' in Chart 1.

CHART 1

| | 'POULrim' | 'POULbero' |
|---|---|---|
| Size of open bloom. | 100–120 mm. | 110–120 mm. |
| Color of top surface of open flower. | Blend of Orange Group 29B–29C. | Red Group 40B, suffused with Red Group Red Group 41B and Yellow-Orange Group 14C. |
| Petalage. | Double, 25–30 petals. | Double, 20–23 petals. |

Parents:

*Seed parent.*—Unnamed seedling.

*Pollen parent.*—Unnamed seedling.

Classification:

*Botanical.*—*Rosa hybrida.*

*Commercial.*—Hybrid Tea.

FLOWER AND FLOWER BUD

Blooming habit: Continuous.

Flower bud:

*Size.*—Upon opening, 35 mm in length from base of receptacle to end of bud.

*Bud form.*—Long and pointed ovoid.

*Bud color.*—As sepals unfold, underlying color is Yellow-Green 154B with areas of color Orange-Red 34A and intonations of Orange-Grey 24B. At ¼ opening, outer bud is Red group 32B on both upper and lower surfaces. Center bud is Orange Group 25B on upper and lower surfaces.

*Sepals.*—Yellow-Green Group 144B on outer side. Inner side is Yellow-Green Group 144D. Anthocyanin present on outer side of 2–3 sepals of Greyed-Purple Group 184A. Weak foliaceous appendages on three of the five sepals. Surfaces of sepals slightly pubescent. A limited number of stipitate glands are present along margins of sepals. Sepals are 25 to 30 cm long and 12 to 13 cm wide. Apex shape is cirrose. Sepal base is flat.

*Receptacle.*—Surface: Smooth. Shape: Broadly funnel. Size: Small. 8 mm (l) ×12 mm (w). Color: Yellow-Green Group 144B.

*Peduncle.*—Surface: Shiny, smooth. Length: 90–130 mm average length. Color: Yellow-Green Group 144B with anthocyanin present on nearly all peduncles observed in tone of Greyed-Purple Group 184A–B). Strength: Strong.

*Borne.*—Generally with 3–5 buds per flowering stem.

Flower bloom:

*Fragrance.*—Strong fruit scent with tones of pears, apples, and black tea.

*Duration.*—The blooms have a duration on the plant of approximately 4 to 6 days.

*Size.*—Medium to large for a hybrid tea rose. Average flower diameter is 100–120 mm when open.

*Form.*—Shape of flower when viewed from the side: Upon opening, upper part: Convex. Upon opening, lower part: Convex. Open flower, upper part: Flat to Flattened Convex. Open flower, lower part: Flat.

*Petalage.*—Double, with 25–30 petals under normal conditions with 1–3 petaloids.

Color:

*Upon opening, petals.*—Outermost petals: Margins of upper surface exhibits intonations of Red Group 42A. Upper Surface: Blend of Orange Group 25B and 25C. Reverse Side: Orange Group 29D. Innermost petals: Upper Surface: Orange Group 25A. Reverse Side: Orange Group 24C.

*Upon opening, basal petal spots.*—Outermost petals: Outer Side: Yellow Group 2C. Inner Side: Yellow Group 6B. Innermost petals: Outer Side: Yellow Group 2C. Inner Side: Yellow Group 6A.

*After opening, petals.*—Outermost petals: Margins of upper surface exhibits intonations of Red Group 42A. Upper Surface: Blend of Orange Group 29B–29C. Reverse Side: Orange Group 29C. Innermost petals: Upper Surface: Blend of Orange Group 25C and 26D. Reverse Side: Orange Group 23D and 24D.

*After opening, basal petal spots.*—Outermost petals: Outer Side: Yellow Group 2D. Inner Side: Yellow Group 6C. Innermost petals: Outer Side: Yellow Group 2D. Inner Side: Yellow Group 4A.

General tonality: On open flower blend of Greyed-Orange 170C, Orange 29A with intonations of Red Group 39A. No change in the general tonality at the end of the 3–4$^{th}$ day. Afterwards, general tonality is a blend of Orange Group 29A and 29B with intonations of Red Group 39B.

Petals:

*Petal reflex.*—Petals reflexed. Outermost petals double reflexed.

*Petal edge.*—Entire with undulation.

*Shape.*—Obovate. Apex is cuspidate.

*Petaloids.*—4–8 petaloids. Petaloids are 5 to 7 mm long and 3 to 5 mm wide. Petaloid coloration is Yellow Group 2D on both outer and inner sides. Texture is smooth.

*Texture.*—Thick and smooth.

*Arrangement.*—Imbricated.

Reproductive organs:

*Pistils.*—Quantity: 20 to 25. Length: 4 to 5 mm.

*Pollen.*—Color: Yellow-Orange Group 14B. Quantity: Average.

*Anthers.*—Size: 2 to 3 mm. Color: Immature: Green-Yellow Group 1B. Margins Greyed-Red Group 180A. Mature: Brown Group 200A. Quantity: 25 to 30.

*Filaments.*—Color: Yellow-Orange Group 14B. Length: 4 to 5 mm.

*Stigmas.*—Located at same level as anthers. Color: Yellow-Green Group 145D.

*Styles.*—Color: Green-White Group 157A. Other intonations: Below stigma, Red-Purple Group 57C.

*Hips.*—None observed.

PLANT

Plant growth: Vigorous, upright to bushy. When grown as a budded field grown plant on multiflora understock, the average height of the plant itself is 90 cm and the average width is 75 cm.

Stems:

*Color*.—Young wood: Green Group 143A. Older wood: Green Group 138A.

*Thorns*.—Incidence: 8 to 10 thorns per 10 cm of stem. Size: Average length: 6 mm–8 mm. Color: Yellow-Green Group 153D. Some intonations of Greyed-Red Group 178B. Shape: Deeply concave.

*Surface*.—Young wood: Smooth. Older wood: Smooth.

Plant foliage: Normal number of leaflets on leaves in middle of the stem: 5 leaflets.

*Leaf size*.—Medium. 120–130 mm (l)×110–120 mm (w).

*Quantity*.—Very abundant.

*Color*.—Upper Leaf Surface: Green Group 147A. Lower Leaf Surface: Green Group 138A–B. Juvenile foliage: Upper surface is Green Group 137A. Lower surface is Green Group 138C. Anthocyanin: Strong intonations throughout the growing season on all new growth. Anthocyanin is Greyed-Purple Group 183B. Location: Leaflets (upper and lower), stems, petiole, rachis and sepals.

Plant leaves and leaflets:

*Stipules*.—Size: 15 mm–20 mm. Color: Green Group 143A. Stipitate glands: On margins of stipules.

*Petiole*.—Length: 25 mm–30 mm. Color: Green Group 137A. Underneath: With several small prickles. Margins: With stipitate glands.

*Rachis*.—Color: Green Group 137A. Underneath: With several small prickles. Margins: With stipitate glands.

*Leaflet*.—Leaflet: Edge: Serrated. Shape: Ovate. The leaflet's apex is acuminate. The leaflet's base is rounded. Arrangement: The leaflets are arranged in an odd-pinnate formation. Venation: The leaflets are veined in a reticulate pattern. Texture: Upper side of leaflet is glossy. Lower side of leaflet is matte. Leaflet is thick.

Disease resistance: Above average resistance to mildew and rust under normal growing conditions in Jackson County, Oreg.

Winter hardiness: 'POULrim' has been found to be resistant to damage from cold in USDA Zone 8 and USDA Zone 7.

We claim:

1. A new and distinct variety of rose plant of the hybrid tea class, substantially as herein illustrated and described as a distinct and novel rose variety due to its abundant, copper/apricot-colored flowers, vigorous and compact growth, and disease resistance.

* * * * *

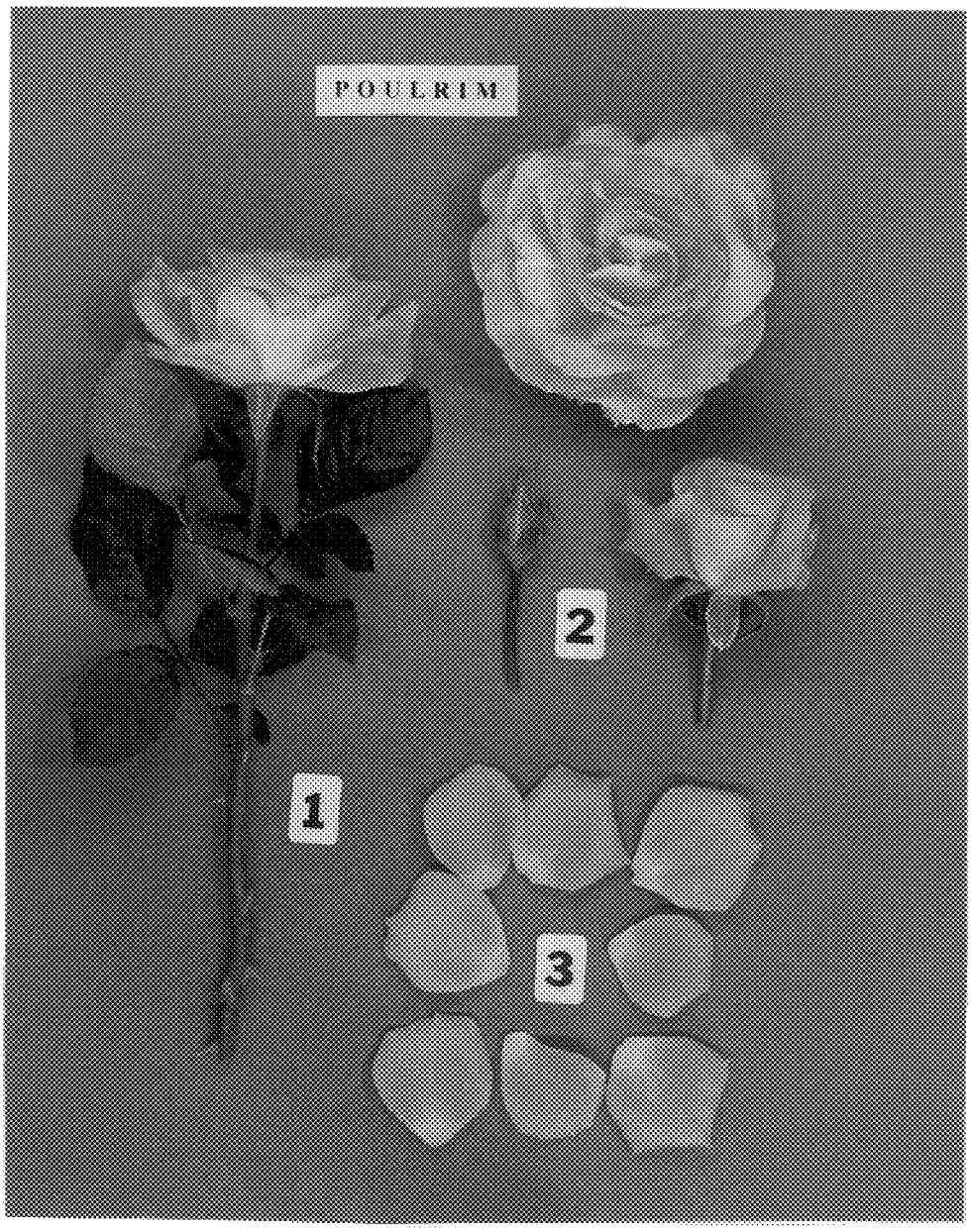
POULRIM
1
2
3

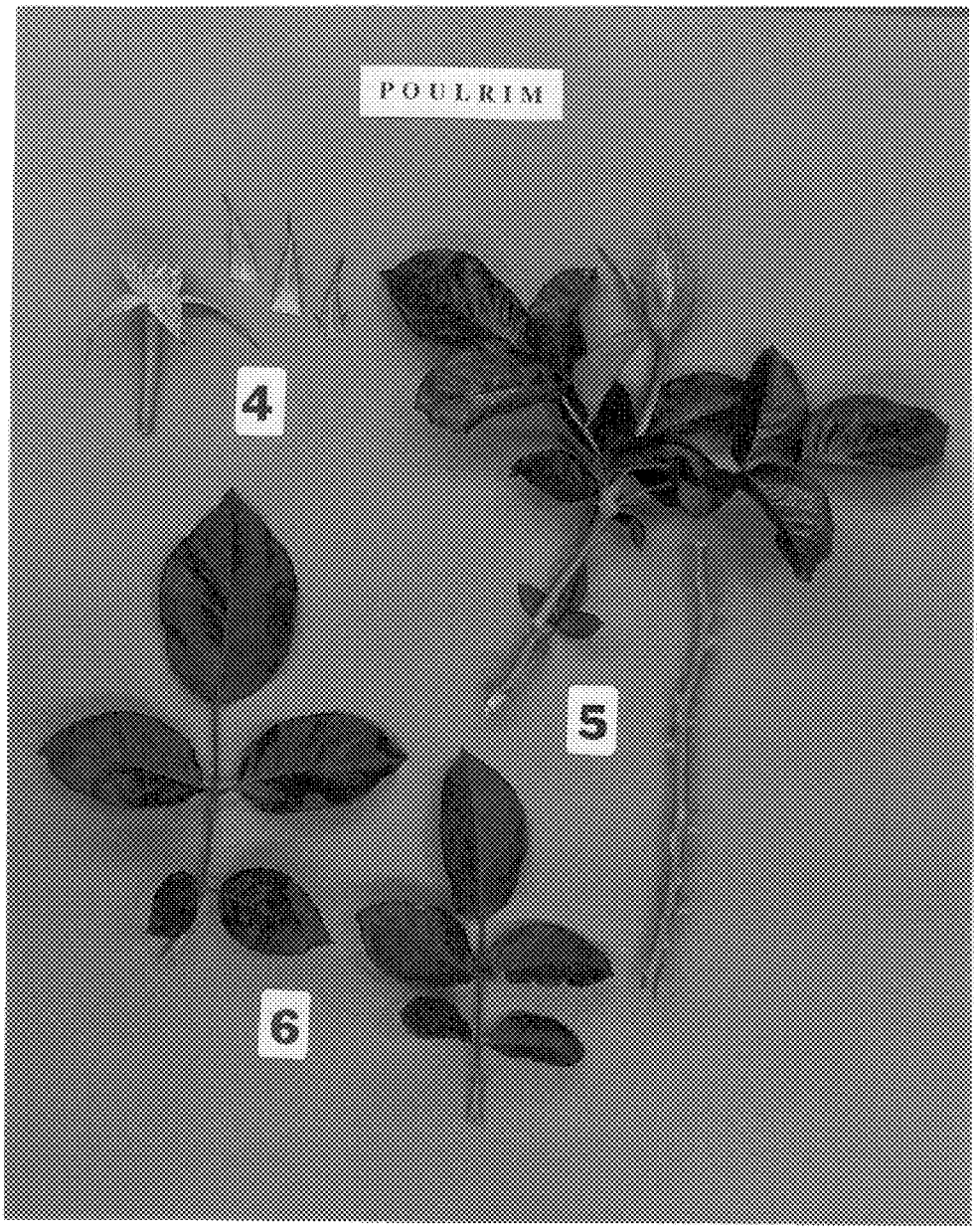
POULRIM
4
5
6